US007677119B2

(12) United States Patent
Garel

(10) Patent No.: US 7,677,119 B2
(45) Date of Patent: Mar. 16, 2010

(54) SYSTEM FOR USING A DEVICE FOR PICKING UP SAMPLES IN A SOIL OR MATERIAL WITH POWDERY OR GRANULAR NATURE

(75) Inventor: Bertrand Garel, La Membrolle sur Choisille (FR)

(73) Assignee: Agro-Systemes, S.A., La Membrolle sur Choisille (FR)

( * ) Notice: Subject to any disclaimer, the term of this patent is extended or adjusted under 35 U.S.C. 154(b) by 8 days.

(21) Appl. No.: 11/126,403

(22) Filed: May 11, 2005

(65) Prior Publication Data

US 2005/0252312 A1 Nov. 17, 2005

(30) Foreign Application Priority Data

May 17, 2004 (FR) .................................. 04 05367

(51) Int. Cl.
*G01N 1/0416* (2006.01)
(52) U.S. Cl. .................................................. 73/864.45
(58) Field of Classification Search .............. 73/864.41, 73/864.43, 864.44, 864.45; 175/20, 58
See application file for complete search history.

(56) References Cited

U.S. PATENT DOCUMENTS 3,596,719 A * 8/1971 Koziski ........................ 175/20
5,004,055 A * 4/1991 Porritt et al. .................. 175/20
5,435,399 A * 7/1995 Peterson et al. ............... 175/20
6,016,713 A * 1/2000 Hale ........................ 73/864.45
6,237,429 B1 * 5/2001 Melnyk .................... 73/864.45
2002/0148306 A1 * 10/2002 Garel ....................... 73/864.43

FOREIGN PATENT DOCUMENTS

FR 2 562 665 10/1985
FR 2 702 563 9/1994

* cited by examiner

*Primary Examiner*—Robert R Raevis
(74) *Attorney, Agent, or Firm*—Nixon & Vanderhye PC

(57) ABSTRACT

The invention relates to a system for using a device for picking up samples in a soil or a material with a granular/powdery nature, said device comprising a vertical stem provided with a groove for collecting the picked-up sample, on the edge of which a lip is formed for scraping the soil or the material to be picked up.

A power-driven system is provided for moving the picking-up device down into the soil/material to be picked up, guiding during this downward movement being provided by vertical guiding means of the picking-up device. A power-driven system is also provided for rotating the picking-up device in the soil/material to be picked up, in order to allow scraping of the soil or material to be picked up by the scraping lip, the upward movement and the collection of the scraped soil/material in the groove of the picking-up device.

15 Claims, 3 Drawing Sheets

SYSTEM FOR USING A DEVICE FOR PICKING UP SAMPLES IN A SOIL OR MATERIAL WITH POWDERY OR GRANULAR NATURE

FIELD OF TECHNOLOGY

The present invention relates to a system for using a device for picking up samples in a soil or a material with a granular or powdery nature, such as an auger for picking up cores on a certain height of soil.

The present invention relates to a system for using a device for picking up samples in a soil or a material with a granular or powdery nature, such as an auger for picking up cores on a certain height of sol.

BACKGROUND

A device for picking up samples in a material with a granular or powdery nature, consisting of a stem in which a channel for collecting material to be picked up is recessed, is known in the prior art from document WO 01/92 847. A scraping lip is formed along the channel. By rotating the device by means of a flywheel located at the upper end of the stem, the material may be collected into the channel. The stem is provided at its lower end, with a nose cone allowing the device to penetrate into the soil.

From documents WO 01/92 847 and FR 2 845 305. It is known how to use a hammer cooperating with a male or female member of the device for picking up samples, this member being positioned above the stem, for helping the user of the device to drive the latter into the soil or the material to be picked up.

However, this type of devices for picking up samples should be driven into the soil or the material to be picked up, and taken out of the soil or material while being held truly vertically. If this is not the case, for example if it is used by a newcomer, there is the risk that the stem might be twisted and the device for picking up samples might become unusable.

SUMMARY

The object of the present invention is to overcome certain drawbacks of the prior art by proposing a system for using devices for picking up samples which allows these sample pick-up devices to be driven into a soil or a material and to be taken out without any risks of damaging the device and with a minimum effort for the user.

This object is achieved by a system for using a sample pick-up device in a soil or material with a powdery or granular nature, said device comprising a substantially vertical stem provided with a groove for collecting the picked-up material, on the edge of which a lip is formed for scraping the soil or the material to be picked up, said system including at least one first power-driven system for causing the picking-up device to be moved down into the soil or the material to be picked up, characterized in that it comprises means for vertically guiding the picking-up device during its moving down and a second power-driven system for causing rotation of the sampling device in the soil or the material to be picked up, allowing scraping of the soil or the material to be picked up by the scraping lip of the picking-up device and collecting the scraped soil or material in the groove of the picking-up device, said first and second power-driven systems being provided above the stem.

According to another feature, the vertical guiding means of the picking-up device consist of three components:

a ring of a supporting device of the power-driven systems for moving down and rotating the picking-up device, said supporting device being slidably mounted onto a driving member of the rack or winch type held substantially vertically by a bracket, a bore passing through a substantially horizontal supporting plate of the picking-up device, said plate being attached to the supporting device, a bore passing through a substantially horizontal plate attached to the lower end of the bracket.

According to another feature, the supporting device comprises a pinion which co-operates with a plurality of teeth of the rack, said pinion being connected to a crank, the actuation of which allows the supporting device to be moved up along the rack, manually or with a mechanical system of the drill type, this upward movement causing the picking-up device to be moved up by the supporting plate of the picking-up device.

According to another feature, the power-driven system for rotating the picking-up device is connected to a mandrel holding the upper portion of a sleeve, the lower portion of said sleeve co-operating with the upper portion of the picking-up device in order to drive it into rotation.

According to another feature, the lower portion of the sleeve is of a shape complementary to a non-cylindrical recess provided in the female component attached above the stem of the picking-up device.

According to another feature, the power-driven system for moving down the picking-up device into the soil or the material to be picked up, is a chipper, the picking-up device being provided with a damping component at its upper end.

According to another feature, the power-driven system for moving down the picking-up device and the power-driven system for rotating the picking-up device are enclosed in a cover provided with a shoulder pressing against the ring of the supporting device.

According to another feature, the system is attached to a vehicle to facilitate its transport, the bracket including a free rotationally mounted bar on a substantially horizontal shaft of the vehicle, allowing the system to pivot around this shaft between a vertical position and a tilted position.

According to another feature, the tilted position of the system is defined by a stop, the system being blocked in this position by an attachment system.

According to another feature, the system comprises a handle facilitating the tilting of the system by a user between the vertical and tilted positions.

According to another feature, the groove includes three faces substantially perpendicular to each other forming a channel, a profiled component being removably attached in said channel for collecting the sample.

Another object of the invention is to propose a method for applying the system according to the invention.

This object is achieved by the method, characterized in that it comprises at least the following steps:

vertically positioning of the system at the location where the sampling should be performed, vertically moving down the picking-up device into the soil or the material to be picked up by means of the power-driven system for moving down the picking-up device, to a maximum until the groove of the stem of the picking-up device is completely driven into the soil or material, vertical support being provided by means for vertically guiding the system, rotating of the picking-up device by the power-driven system for rotating the picking-up device so as to pick up samples by the scraping lip and to collect them in the groove of the picking-up device, moving up the picking-up device by actuating the crank or an equivalent mechanical device until the head of the picking-up device has completely moved out of the soil or material, extracting the sample picked up from the groove by means of a suitable tool and storing it in a container intended for this purpose.

According to another feature, the step for vertically positioning the system consists of having the latter tilt from its tilted position to its vertical position after an unlocking step of the attachment system.

According to another feature, the step for extracting the sample is preceded by a step for tilting the system from its vertical position to its tilted position.

BRIEF DESCRIPTION OF DRAWINGS

Other features and advantages of the present invention will appear more clearly upon reading the description hereafter, made with reference to the appended drawings, wherein.

DETAILED DESCRIPTION

Figure 1:
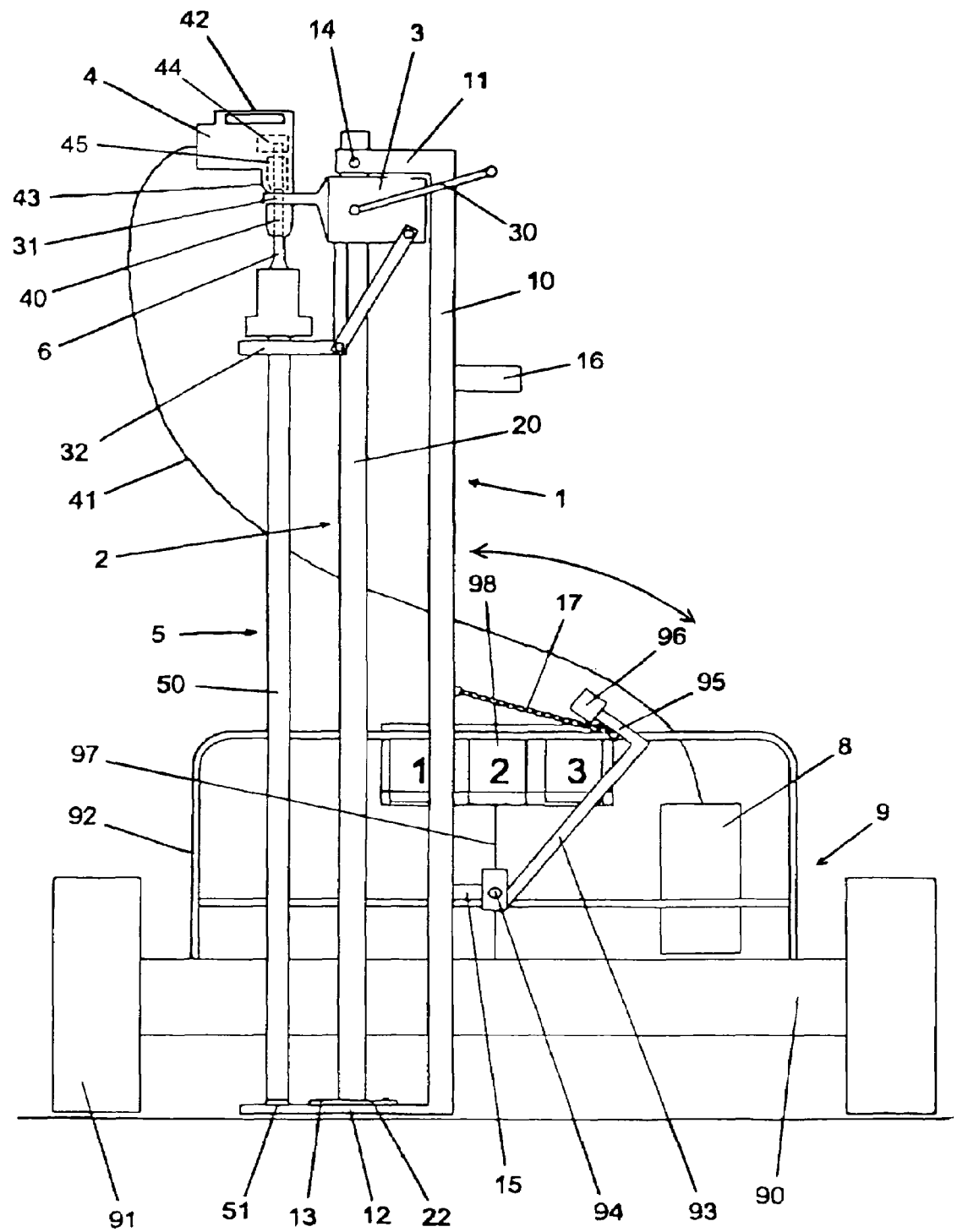
FIG. 1 illustrates a profile view of the system according to the invention.

The system for using sample pick-up devices in a soil or material with a granular or powdery nature according to the invention, consists of a bracket (1) on which is attached a rack (2) along which a device (3) for supporting a chipper block/rotary tool (4) may slide, which supporting device (3) also supporting the device (5) for picking up samples. Alternatively, the rack (2) may be replaced with an equivalent driving member, for example a winch capable of sliding along the bracket (1).

The bracket (1) consists of a substantially vertical bar (10) at the upper end of which two substantially horizontal bars (11), and parallel to each other and spaced apart from each other by a distance equivalent to the width of the rack (2), are for example attached by being welded thereon. A substantially horizontal plate (12) is for example attached, by being welded thereon, to the lower end of the vertical bar (10) of the bracket (1), so as to form an "L" with the latter.

The rack (2) consists of a bar (20) with a substantially rectangular section, provided on at least one of its faces with a plurality of substantially horizontal teeth (21) positioned one above the other over the whole height of said bar (20) with a rectangular section. The teeth (21) are spaced apart from each other by a constant distance. A substantially horizontal plate (22) is for example attached, by being welded thereon, to the lower end of the bar (20) with a rectangular section.

The bar (20) with a rectangular section of the rack (2) is positioned parallel to the vertical bar (10) of the bracket (1), the plate (22) of the rack (2) pressing against the plate (12) of the bracket (1) and the upper end of the rack (2) being introduced between both mutually parallel horizontal bars (11) of the bracket (1). The plate (22) of the rack (2) is made integral with the plate (12) of the bracket (1) by screwing at least two screws (13) each penetrating at the same time into a bore made in the plate (22) of the rack (2) and into a tapped hole of the plate (12) of the bracket (1). The upper end of the rack (2) is attached to horizontal bars (11) of the bracket (1) by means of pin (14) or an equivalent component passing both through a bore made in the width of the bar (20) with a rectangular section of the rack (2) and through two bores each made into the thickness of each of the horizontal bars (11) of the rack (1).

Figure 2:
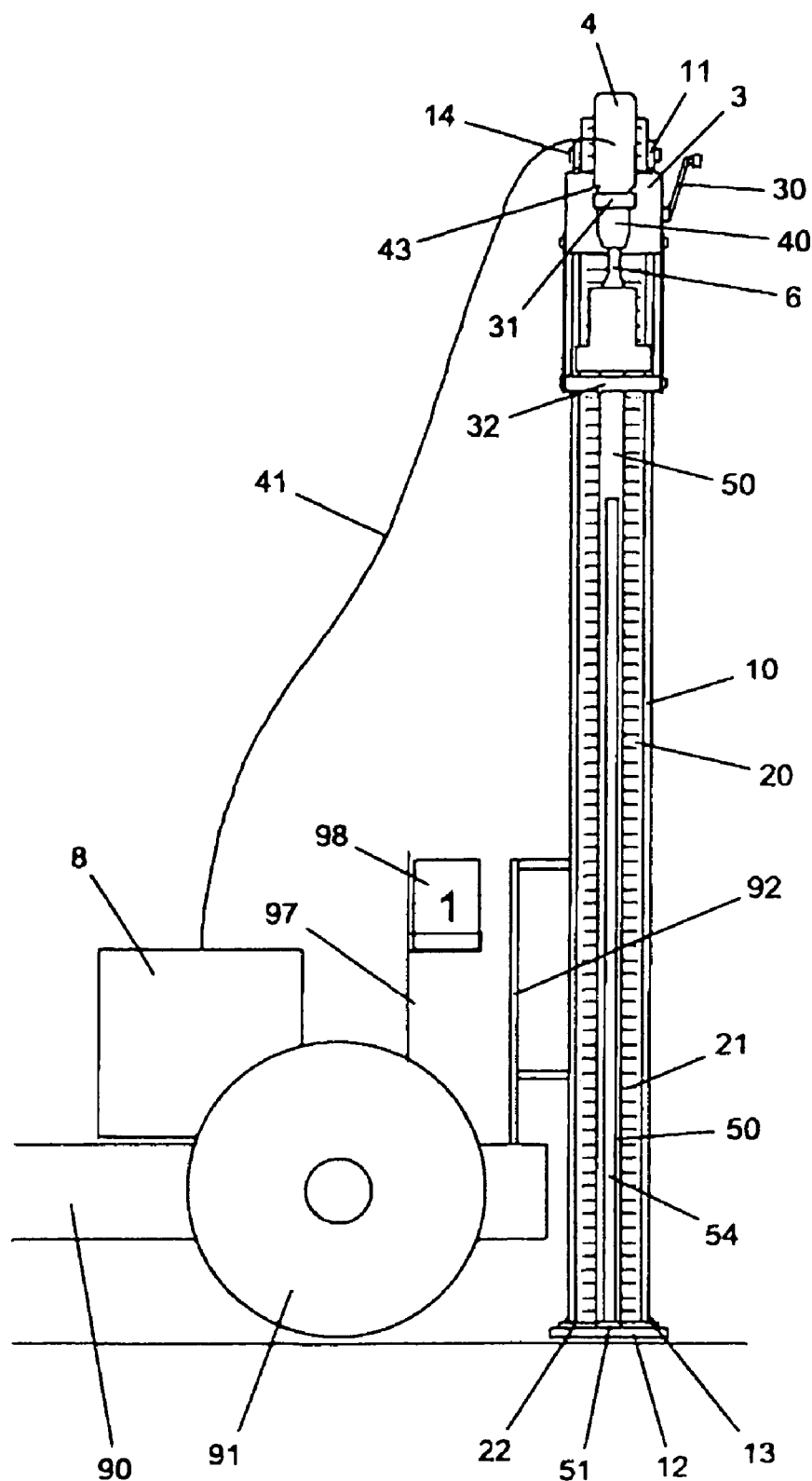
FIG. 2 illustrates a front view of the system according to the invention.

The supporting device (3) is translationally movably mounted onto the rack (2). It includes at least one pinion (not shown) engaging into the teeth (21) of the rack (2) and connected to a crank (30). Such a crank may for example be actuated by a user of the system according to the invention to move up or down the picking-up device (5). In one embodiment of the invention, actuation of the crank (30) may trigger a mechanical system of the drill type, facilitating the moving up or down of the supporting device (3). A substantially horizontal ring (31) is attached to the supporting device (3), preferably in alignment with the bracket (1) and the rack (2), as illustrated in FIGS. 1 and 2. This ring (31) supports the chipper block/rotary tool (4). A substantially horizontal plate (32) is attached onto the supporting device (3). This plate (32) is provided with a through-bore (320) substantially located in the axis of the ring (31) of the supporting device (3).

Figure 4:
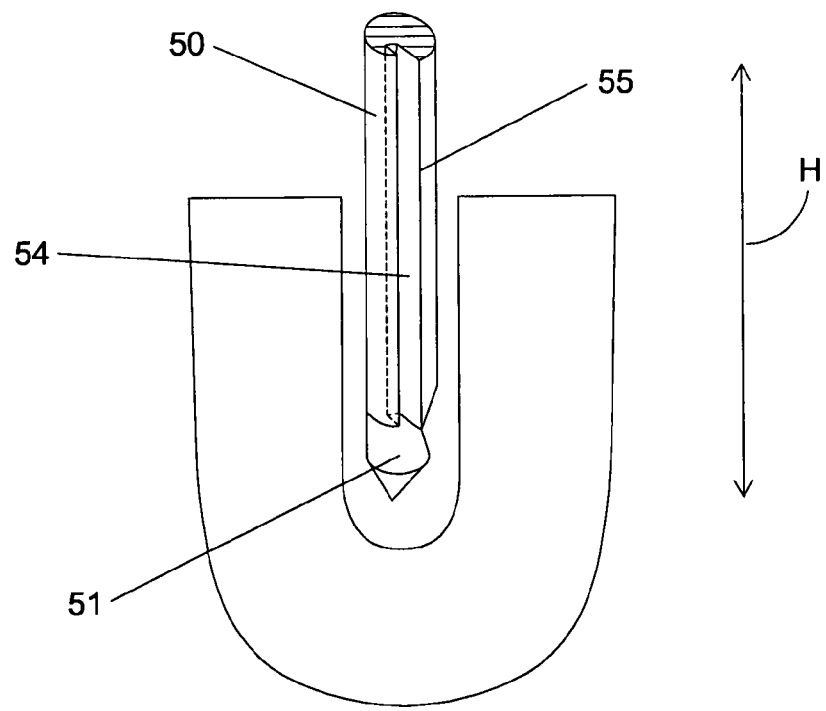
FIG. 4 illustrates the lower portion of a device for picking up samples partly driven into a soil.

The picking-up device (5) to be used with the system according to the invention should include a vertical stem (50) at the lower end of which a head (51), particularly visible in FIG. 4, is attached, for example screwed thereon, said head (51) allowing the picking-up device to be driven into the soil or the is material to be picked up with minimum friction. The stem (50) extends between its lower end and its upper end over a height (H) between 20 and 120 cm, so that it is possible to pick up soil or material at a significant depth. The head (51) of the picking-up device (5) preferably has a conical nose shape, the diameter of which is to be adapted depending on the composition and the moisture level of the soil or material to be picked up. The stem (50) of the picking-up device (5) is welded at its upper end to a substantially horizontal disc (52). This female component (53) at its center is provided with a non-cylindrical sectional recess, for example a square recess, provided for receiving a sleeve (6) with a lower section complementary to the recess, this sleeve (6) being removably attached to the chipper bloc/rotary tool (4). In an alternative embodiment, the female component (53) is replaced with a male component with a non-cylindrical, for example a square section, and the lower end of the sleeve (6) is replaced with a female component at its center, provided with a non-cylindrical, for example a square sectional recess, complementary to the male component.

Figure 3:
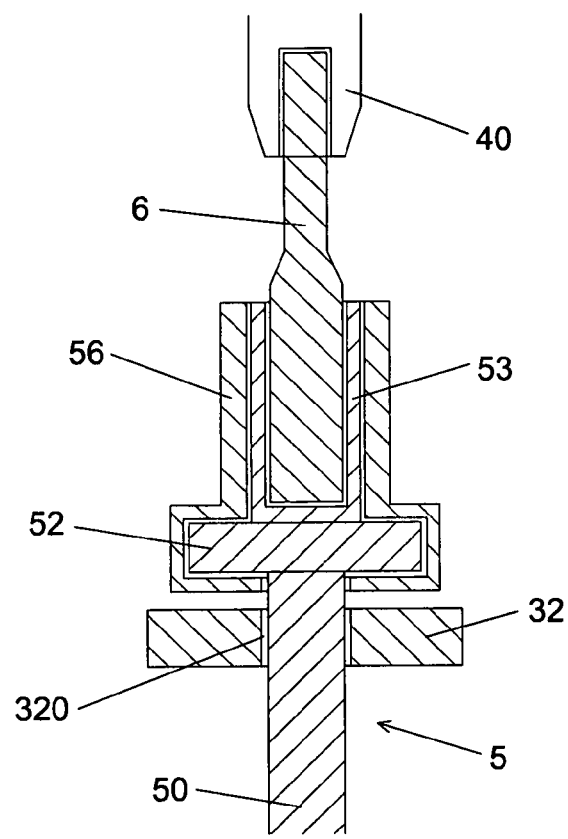
FIG. 3 shows a detailed sectional view of the connection between the system according to the invention and a device for picking up samples.

The stem (50) of the picking-up device (5) is introduced into the bore (320, FIG. 3) of the plate (32) of the supporting device (3). The diameter of the disc (52) of the picking-up device (5) being larger than the diameter of the bore (320) of the plate (32) of the picking-up device (3), the disc (52) pressing against the plate (32). A damping component (not shown), preferably in plastic, is provided at the upper end of the picking-up device (5) positioned around the disc (52) and the female component (53) illustrated in FIG. 3, in order to avoid metal-metal contacts between the disc (52) of the picking-up device and the plate (32) of the supporting device (3) and to damp mutual mechanical impacts during the use of the system according to the invention, particularly upon moving the picking-up device down into the soil or material to be picked up.

The lower end of the stem (50) passes through a bore made in the plate (12) of the bracket (1), said bore being located in the axis of the ring (31) of the supporting device (3) and in that of the bore (320) of the plate (32) of the supporting device (3). In this way, the stem (50) of the picking-up device (5) is vertically guided by three points during its upward and downward movement, so as not to risk damaging it, by twisting it for example.

As shown in FIG. 4, the stem (50) of the picking-up device (5) includes a groove (54) on the major part of the length of the stem (50). The groove (54) includes three faces disposed angularly to each other thereby forming a channel (see vertical solid and dashed lines). The faces are not of the same width, thereby forming a protruding portion (55) which forms a scraping lip for scraping the earth surrounding the picking-up device (5) when the latter is driven into the soil and rotated by means of the chipper block/rotary tool (4). The materials which accumulate in the groove (54) of the picking-up device from the picked-up sample, which is recovered after having removed the picking-up device (5) from the soil. In one embodiment of the invention, the groove (54) is fitted with a profiled component (not shown) removably attached in the channel for collecting the picked-up sample. With the profiled component, it is possible to easily extract the picked-up sample from the groove (54), for example by removing attachment clips from this profiled component.

The chipper block/rotary tool (4) comprises a mandrel (40) provided for receiving and holding the upper end of the sleeve (6). The mandrel is connected to a rotary tool 45 comprised in the chipper, block/rotary tool (4), which allows the sleeve (6) to be rotated around its axis, the mandrel's axis (40) coinciding with the axis of the picking-up device (5), rotation of the mandrel then causing the rotation of the picking-up device (5). The chipper block/rotary tool (4) also comprises a chipper 44 which plays a similar role to that of the hammer known from the prior art, by regularly hammering the picking-up device (5) in order to drive it into the soil or material to be picked up. The chipper block/rotary tool (4) may be electrically powered via an electrical wire (41) connected to a motor (8). The power supply of the chipper block/rotary tool (4) may alternatively also be pneumatic, thermal or hydraulic. The user of the invention according to the invention may control the starting up of the chipper and/or rotary tool of the chipper block/rotary tool (4), for example by means of buttons located on a handle (42) of said chipper block (4). Also, the motor (8) includes at least one start/stop switch. In an alternative embodiment, the chipper and the rotary tool are not part of a block but are independent of each other.

The chipper block/rotary tool (4) preferably includes a cover in which the upper end of the mandrel (40), the rotary tool 45 and the chipper 44 are enclosed. The part of the cover enclosing the upper end of the mandrel (40) is introduced into the ring (31) of the supporting device (3), so that the axis of the mandrel (40) is vertical. The cover of the chipper block/rotary tool (4) includes a shoulder (43) above its portion enclosing the upper end of the mandrel (40) this shoulder pressing against the edges of the ring (31) of the supporting device (3).

When the system according to the invention is ready to use or being used, the plate (12) of the bracket (1) is positioned in close vicinity of the soil or material to be picked up. When the picking-up device (5) is not used, the supporting device (3) is moved up sufficiently along the rack so that the lower end of the head (51) of the picking-up device is not located below the lower surface of the plate (12) of the bracket (1). This position for example corresponds to a position for which the supporting device (3) is located against the horizontal bars (11) of the bracket (1) as illustrated in FIGS. 1 and 2.

The system according to the invention is preferably attached onto a vehicle (9) for facilitating its transport. For example, the vehicle (9) is a quad or a golf caddy, but not in a non-limiting way. The vehicle (9) includes at least a chassis (90) supported by wheels (91) or gliders, as well as a system for actuating and controlling the vehicle, such as for example a motor, a flywheel, accelerating and braking means, steering means, etc. . . . A frame (92), for example a tubular frame, supporting the system according to the invention is attached onto the chassis (90) of the vehicle (9). A bar (93), tilted relatively to the vertical, is attached to said frame (92), substantially in the alignment of the bracket (1) of the rack (2) and of the picking-up device (5). A substantially horizontal shaft (94) is attached to the lower end of this tilted bar (93). A bar (15) provided with a through-bore, perpendicularly attached to the vertical bar (10) of the bracket (1), for example by being welded thereon, may freely pivot around this shaft (94), the longitudinal axis of shaft 94 is perpendicular to the sheet of paper depicting FIG. 1, in the plane of symmetry of the bracket (1) and the rack (2), which enables the system according to the invention to be tilted relatively to the vertical for its transport. The tilted bar (93) of the vehicle (9) at its upper end, includes a stop (95) against which the system according to the invention will press so as to assume a tilt substantially parallel to said tilted bar (93), the direction of tilt being shown by the arrow in FIG. 1. An attachment system (96) of the system according to the invention is attached to the free end of this stop (95) in order to maintain the system according to the invention in its tilted position during its transport, in the tilted position vertical bar (10) abut against attachment system (96) of stop (95). In a preferred embodiment of the invention, the system according to the invention is provided with a handle (16) attached on the bracket, for example by being welded thereon, said handle facilitating the tilting by a user of the system according to the invention between its vertical position of use and its tilted position of transport. The system according to the invention is for example connected to the stop (95) of the tilted bar (93) of the vehicle by a chain (17) positioned between the vertical bar (10) of the bracket (1) and said stop (95).

A device (97) for supporting at least one container (98) for collecting collected samples is preferably attached onto the chassis (90) of the vehicle (9). Also, the motor (8) or the hydraulic central system powering the chipper block/rotary tool (4) is attached on the chassis (90) of the vehicle (9).

The picking-up device may easily be dismantled from the system according to the invention so as to be replaced depending on the type of soil or material to be picked up. Thus, the user of the system according to the invention may select a picking-up device, the diameter of the stem of which or even the size of the scraping lip will be adapted to the desired use.

The method for applying the system according to the invention will now be described. The system according to the invention is first brought close to the location on which samples should be taken, for example by means of the vehicle (9) described earlier. The system according to the invention is then tilted from its tilted position to its vertical position by the user with the help of the handle (16) after having unlocked the attachment system (96) of the vehicle (9). Possible replacement of the picking-up (5) device and/or the head (51) should be performed before tilting. The motor (8) of the system according to the invention is then started by the user. The latter then starts up the chipper of the chipper block/rotary tool (4) in order to drive the picking-up device into the soil or material to be picked up. Under the action of the chipper, which will produce erratic impacts on the picking-up device (5) and on the ring (31) of the supporting device (3), the picking-up device (5) is driven into the soil while the supporting device (3) moves down along the rack (2). As soon as the groove (54) of the stem (50) of the picking-up device (5) is completely driven into the soil or as soon as the picking-up device (5) can no longer advance into the soil if it abuts for example on stones, the user stops the chipper. He then starts up the rotary tool of the chipper block/rotary tool (4) so as to rotate the picking-up device in the soil or the material to be picked up, so as to pick up samples by means of the scraping lip (55) and collect them in the groove (54). After a certain number of turns, for example after a number of 10, the user stops the rotary tool. He then actuates the crank (30) or a dedicated motor of the supporting device (3) for moving up the latter along the rack (2), which simultaneously causes the picking-up device (5) to move up by means of the plate (32) attached on the supporting device (3). The user may stop its movement as soon as the lower end of the head (51) of the picking-up device is located below the lower surface of the plate (12) of the bracket (1). The user may then scrape part of the collected earth to remove possible contaminants which may have occurred during the upward movement. In one embodiment, the system according to the invention may then again be tilted into its tilted position. The user may then extract the picked-up sample from the groove (54) by means of a suitable tool and store it in a container (98) provided for this purpose. The attachment system (96) may then be locked if the system according to the invention must again be transported, for example for performing another collection.

It should be obvious to one skilled in the art that the present invention allows embodiments under many other specific forms without departing from the field of application of the invention as claimed. Accordingly, the present embodiments should be considered as an illustration but they may be changed within the field defined by the scope of the enclosed claims, and the invention should not be limited to the details given above.

The invention claimed is:

1. An apparatus for obtaining samples in a soil or material having a powdery or granular nature, said apparatus comprising:
   a picking-up device having a vertical stem provided with a groove intended for collecting the soil or material sample, on the edge of which a lip is formed for scraping the soil or the material to be picked up;
   at least one first power-driven system for causing the picking-up device to be moved down into the soil or the material to be picked up and to be moved up away from the soil or the material to be picked up;
   means for vertically guiding the picking-up device during the downward movement, and for allowing a rotation of the stem around its axis; and
   a second power-driven system for causing the rotation of the stem in the soil or the material to be picked up, allowing scraping of the soil or the material to be picked up, by the scraping lip of the stem, and collection of the scraped-up soil or material in the groove of the stem, said first and second power-driven systems being provided above the stem; and
   a bracket having a plate making a base at its lower end, a bore being made in the plate to provide vertical guidance on the side of the lower end of the stem of the picking-up device; and
   a supporting device movable with respect to the plate along the bracket and having vertical guiding means on the upper side of the picking-up device during the moving down of the picking-up device.

2. The apparatus according to claim 1, wherein the vertical guiding means comprises:
   a ring of the supporting device of the power-driven systems for moving down and rotating the picking-up device, said supporting device being slidably mounted onto a driving member of a rack held by the bracket substantially vertically,
   a bore passing through a substantially horizontal supporting plate of the picking-up device, said plate being fixed to the supporting device; and
   a bore passing through a substantially horizontal plate attached to the lower end of the bracket.

3. The apparatus according to claim 2, wherein the supporting device comprises a pinion which co-operates with a plurality of teeth of the rack, said pinion being connected to a crank, the actuation of which allows the supporting device to be moved up along the rack the upward movement of the supporting device causing upward movement of the picking-up device by means of the supporting plate fixed to the picking-up device.

4. The apparatus according to claim 2, wherein the second power-driven system for rotating the picking-up device being connected to a mandrel holding the upper portion of a sleeve, the lower portion of said sleeve co-operating with the upper portion of the picking-up device for driving it into rotation.

5. The apparatus according to claim 4, wherein the lower portion of the sleeve is of a complementary shape to a non-cylindrical recess provided in a female component attached above the picking-up device.

6. The apparatus according to claim 4, wherein the lower portion of the sleeve is a female component in which a non-cylindrical recess is provided with a complementary shape to the upper portion of the picking-up device.

7. The apparatus according to claim 2, wherein the at least one first power-driven system for moving the picking-up device down into the soil or the material to be picked up comprises a chipper in a chipper block/rotary tool, an upper end of the picking-up device being fixed to the chipper, and the second power-driven system, comprised in the chipper block/rotary tool, being arranged for rotating the picking-up device independently of the moving down of the picking-up device.

8. The apparatus according to claim 2, wherein the second power-driven system for rotating the picking-up device is provided with a shoulder pressing against the ring of the supporting device.

9. The apparatus according to claim 2, wherein the apparatus is attached to a vehicle for facilitating its transport, the bracket and a bar rotationally mounted on a substantially horizontal shaft of the vehicle allowing the systems to pivot around the shaft between a vertical position and a tilted position.

10. The apparatus according to claim 9, wherein the tilted position is defined by a stop.

11. The apparatus according to claim 9, wherein the apparatus further comprises a handle facilitating the tilting of the apparatus between the vertical and tilted positions.

12. The apparatus according to claim 1, wherein the groove includes three faces angularly disposed to each other forming a channel, such that a profiled component can be employed for removing the picked-up soil or material.

13. A method for applying the apparatus according to claim 1, the method comprising:
   vertically positioning the apparatus at a location for the picking-up of soil or material;
   vertically moving down the picking-up device into the soil or the material to be picked up by the at least one first power-driven system until the groove of the stem is completely driven into the soil or material, vertical support being provided by the vertical guiding means;

rotating the picking-up device by the second power-driven system to pick up samples of soil or material by means of the scraping lip and to collect the samples in the groove of the picking-up device;

moving up the picking-up device by actuating a crank until the stem has completely moved out of the soil or material, and extracting the picked-up sample from the groove.

14. The method according to claim 13, wherein vertically positioning the apparatus consists of moving the apparatus from its tilted position to its vertical position.

15. The method according to claim 13, wherein extracting the picked-up sample is preceded by moving the apparatus from its vertical position to its tilted position.

* * * * *